US010765381B2

(12) United States Patent
Okuno et al.

(10) Patent No.: US 10,765,381 B2
(45) Date of Patent: Sep. 8, 2020

(54) RADIATION IMAGING APPARATUS

(71) Applicant: SHIMADZU CORPORATION, Kyoto-shi, Kyoto (JP)

(72) Inventors: Tomoharu Okuno, Kyoto (JP); Masahiro Kawano, Quebec (CA)

(73) Assignee: SHIMADZU CORPORATION, Kyoto (JP)

( * ) Notice: Subject to any disclaimer, the term of this patent is extended or adjusted under 35 U.S.C. 154(b) by 268 days.

(21) Appl. No.: 16/115,766

(22) Filed: Aug. 29, 2018

(65) Prior Publication Data

US 2020/0069260 A1 Mar. 5, 2020

(51) Int. Cl.
*G01T 1/17* (2006.01)
*A61B 6/02* (2006.01)
*A61B 6/00* (2006.01)

(52) U.S. Cl.
CPC .............. *A61B 6/025* (2013.01); *A61B 6/40* (2013.01); *A61B 6/4452* (2013.01); *A61B 6/4464* (2013.01); *A61B 6/46* (2013.01); *A61B 6/5205* (2013.01); *A61B 6/547* (2013.01); *G01T 1/17* (2013.01)

(58) Field of Classification Search
CPC ..... A61B 6/025; A61B 6/4452; A61B 6/5235; A61B 6/547; A61B 6/4429; A61B 6/588; A61B 6/589; G01T 1/17
See application file for complete search history.

(56) References Cited

U.S. PATENT DOCUMENTS

2003/0219101 A1* 11/2003 Tsujii .................. A61B 6/4429
378/205

FOREIGN PATENT DOCUMENTS

| JP | 2002-263093 | 9/2002 |
| JP | 2009-297284 | 12/2009 |
| JP | 2012-100738 | 5/2012 |
| JP | 2013-103002 | 5/2013 |
| WO | WO2015/166575 | 11/2005 |

* cited by examiner

*Primary Examiner* — David P Porta
*Assistant Examiner* — Fani Boosalis
(74) *Attorney, Agent, or Firm* — Andrew F. Young, Esq.; Lackenbach Siegel, LLP (57) ABSTRACT

A radiation imaging apparatus performs pre-shot imaging while considering the imaging condition on the tomosynthesis imaging which can be performed right thereafter without repeating a positioning of the radiation irradiation unit on the tomosynthesis imaging. The protocol for the per-shot imaging is read out. Reading out the protocol is executed by that the operator of operation unit of the console and the console 1 reads out the protocol for the pre-shot imaging from the radiology department information system along with the patient information. Therefore, the imaging condition of the protocol for the continuously executed tomosynthesis imaging is read out while linking the protocol of the pre-shot imaging.

5 Claims, 3 Drawing Sheets

RADIATION IMAGING APPARATUS

CROSS REFERENCE TO RELATED APPLICATIONS

This application relates to, but does not claim priority from, JP 2016-055352 filed Mar. 18, 2016 and published as JP 2017-164426 on Sep. 21, 2017, the entire contents of which are incorporated herein by reference.

FIGURE SELECTED FOR PUBLICATION

FIG. 2

BACKGROUND OF THE INVENTION

Field of the Invention

The present invention relates to a radiation imaging apparatus that performs a tomosynthesis imaging.

Description of the Related Art

With respect to the X-ray imaging apparatus that performs the tomosynthesis imaging for taking the tomographic image of the subject, the X-ray tube irradiates intermittently X-rays toward the X-ray detector while moving the X-ray tube in the body-axis direction of the subject. In such a case, the X-ray detector moves in the opposite direction against the X-ray tube every time once the X-ray irradiation ends. X-ray images, e.g., 74 X-ray images, are obtained by repeating the above action, and such X-ray images are reconstructed to provide a tomographic image by applying a filtered back projection (FBP) to such obtained X-ray images. Such a tomographic image is an image incorporating the tomographic image obtained when the subject is sliced at a cross-section thereof.

A pre-shot imaging is carried out prior to such a tomosynthesis imaging. When carrying out pre-shot imaging, one X-ray image is taken while the X-ray tube and X-ray detector are still. According to such a pre-shot imaging, the positioning of the subject is confirmed, and X-ray conditions, including such as the tube electric current provided to X-ray tube and an imaging time for X-ray imaging and so forth, relative to the tomosynthesis imaging are determined.

Patent Document 1 discloses the radiation imaging apparatus that confirms precisely the imaging position without increasing a radiation dose by displaying at least one of a plurality of radiation images imaged by the radiation detection means instead of carrying out the pre-shoot imaging when a plurality of radiation images is continuously imaged to solve the problems; in which the imaging position on the pre-shooting does not always coincide with the imaging position on the actual tomosynthesis imaging, so that the imaging position is not precisely confirmed, and the radiation dose exposed to the subject increases as much as such a pre-shooting imaging.

In addition, Patent Document 2 discloses a radiation tomographic imaging apparatus that comprises: a radiation source that irradiates a radiation to a subject; a detection means that detects the radiation transmitted through the subject; a radiation source movement means that moves radiation source in the body axis direction of a subject; a radiation irradiation control means controls said radiation source so as to repeatedly irradiate the radiation while said radiation source movement means is moving said radiation source; an image generation means generates a radiation image using a detection signal output from said radiation detection means every radiation irradiation from radiation source; a tomographic image acquisition means that acquires a radiation tomographic image by reconstructing a plurality of radiation images generated by the image generation means; and a possible imaging range calculation means that calculates the possible imaging range of the radiation detection means, which is the positional range of the radiation detection means, in which the radiation source is within the movable range of the radiation source and the detection means can acquire the radiation tomographic image based on a group consisting of parameters comprising; an imaging distance from the focal point of the radiation source and the radiation detection means, the irradiation swing angle that is the swing angle of the radiation source while the radiation irradiation means allows the radiation source repeatedly irradiating the radiation, and the movable range of the radiation source. According to the radiation tomographic imaging apparatus disclosed in Patent Document 2, it is preventable in advance that the radiation source such as an X-ray tube moves outside of the movable range and interferes with such as the floor surface.

RELATED PRIOR ART DOCUMENTS

Patent Document

Patent Document 1: JP Patent Published 2009-240435 A1
Patent Document 2: WO2015/166575 A1

ASPECTS AND SUMMARY OF THE INVENTION

Objects to be Solved

As set forth above, when the pre-shot imaging is carried out, the pre-shot imaging and the tomosynthesis imaging are continuously performed. Conventionally, in such a case, at the time when the pre-shot imaging is performed, the imaging distance at the time when the tomosynthesis imaging is subsequently performed is not generally recognized (i.e., unknown). Specifically, when performing the pre-shot imaging, a protocol for the pre-shot imaging is selected and the imaging condition for the pre-shot imaging is displayed. In addition, when performing the tomosynthesis imaging, a protocol for the tomosynthesis imaging is selected and the imaging condition for the tomosynthesis imaging is displayed. Conventionally, therefore, the operator is unaware of the imaging condition for the tomosynthesis imaging when performing the pre-shot imaging. Whereas each imaging distance on the pre-shot imaging and the tomosynthesis imaging must be the same as one another. Accordingly, the operator must select again the imaging protocol for the pre-shot imaging following confirming the imaging distance of the tomosynthesis imaging by selecting the imaging protocol thereof at the operation element.

In addition, when the tomosynthesis imaging is carried out, the movable range of the X-ray tube is mechanically restricted. When the tomosynthesis imaging is performed, the X-ray tune moves with some angle relative to the X-ray detector to irradiate the X-ray, so that the position of the X-ray tube may be out of the movable range thereof depending on the angle of the X-ray tube and the position of the X-ray detector. Particularly, when the imaging distance is long to reduce the magnification percentage of the image obtained by the X-ray imaging, when the a large tomographic angle is set to thin the tomography thickness, or when the position of the tomographic center is set up closer to the X-ray detector in the case of which the X-ray detector moves, the movement distance of the X-ray tube is large, so that the likelihood of that the X-ray tube is out of the movable range thereof becomes higher. In addition, when the imaging period of time for the tomosynthesis imaging shortens, the movement rate of the X-ray tube increases and the distance (entrance length) for acceleration of the X-ray tube is longer, so that the likelihood of that the X-ray tube is out of the movable range thereof becomes higher as well as the above case. Therefore, when the following tomosynthesis imaging is performed, the required positional arrangement of the X-ray tube is going out of the movable range of the X-ray tube in case depending on the arrangement of the X-ray tube and the X-ray detector when the pre-shot imaging is performed, and in such a case, the arrangement of the X-ray tube and the X-ray detector must be changed.

The purpose of the present invention is to solve the above object and particularly, to provide the radiation imaging apparatus that performs the pre-shot imaging while considering the imaging condition on the tomosynthesis imaging, wherein when performing the tomosynthesis imaging, the tomosynthesis imaging can be performed right thereafter without repeating positioning of the radiation irradiation unit on the tomosynthesis imaging.

Means for Solving the Problem

According to the invention claimed in Claims, a radiation imaging apparatus comprises: a radiation irradiation unit; a radiation detector that detects a radiation that is irradiated from the radiation irradiation unit and transmits through a subject; a radiation irradiation unit movement mechanism that moves the radiation irradiation unit in a body axis direction of the subject and oscillates the radiation irradiation unit to adjust the radiation irradiation direction, which is a facing direction to the radiation detector, along with the movement of the radiation irradiation unit; wherein the radiation imaging apparatus performs a tomosynthesis imaging that carries out the imaging multiple times relative to the subject while moving the radiation irradiation unit following performing a pre-shot imaging, in which an imaging relative to the subject is carried out while the movement of the radiation irradiation unit is suspending; and the radiation imaging apparatus further comprises: a protocol storage that stores a plurality of protocols corresponding to the imaging; a display that displays an imaging condition corresponding to a presently selected from the plurality of protocols; and a control unit that displays the imaging condition for the tomosynthesis imaging along with the imaging condition for the pre-shot imaging on the display when the protocol for the pre-shot imaging is selected in the case of that the pre-shot imaging and the tomosynthesis imaging are registered in the temporally-continuous protocol among the plurality of protocols stored in the protocol storage.

According to another invention claimed in the Claims, a radiation irradiation unit; a radiation detector that detects a radiation that is irradiated from the radiation irradiation unit and transmits through a subject; a radiation irradiation unit movement mechanism that moves the radiation irradiation unit in a body axis direction of the subject and oscillates the radiation irradiation unit to adjust the radiation irradiation direction, which is a facing direction to the radiation detector, along with the movement of the radiation irradiation unit; wherein the radiation imaging apparatus performs a tomosynthesis imaging that carries out a plurality of imagings relative to the subject while moving the radiation irradiation unit following performing a pre-shot imaging, in which an imaging relative to the subject is carried out while the movement of the radiation irradiation unit is suspending; and the radiation imaging apparatus further comprises: a protocol storage that stores a plurality of protocols corresponding to the imaging; a control unit that determines whether the tomosynthesis imaging is feasible or not in the basis of the imaging condition on the pre-shot imaging by reading out the imaging condition for the tomosynthesis imaging along with the imaging condition for the pre-shot imaging when the protocol for the pre-shot imaging is selected in the case of that the pre-shot imaging and the tomosynthesis imaging are registered in the temporally-continuous protocol among the plurality of protocols stored in the protocol storage.

According to an aspect of another invention claimed in the claims, the tomosynthesis imaging condition comprises an imaging distance and the tomographic angle.

According to an aspect of another invention claimed in the claims, the tomosynthesis imaging condition further comprises an imaging time-duration.

According to an aspect of the invention claimed in the claims, the tomosynthesis imaging condition further comprises a tomographic center.

Effects of the Present Invention

According to the inventions claimed in claims, when reading out the imaging condition of the pre-shot imaging prior to the pre-shot imaging, the imaging condition for the next tomosynthesis imaging is read out and displayed, or it is determined whether imaging is feasible or not, so that the pre-shot imaging is carried out while considering the imaging condition for the tomosynthesis imaging and also, the tomosynthesis imaging can be performed immediately without repeating positioning of the radiation irradiation unit on the tomosynthesis imaging. Accordingly, the tomosynthesis imaging can be efficiently performed.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Figure 1A:
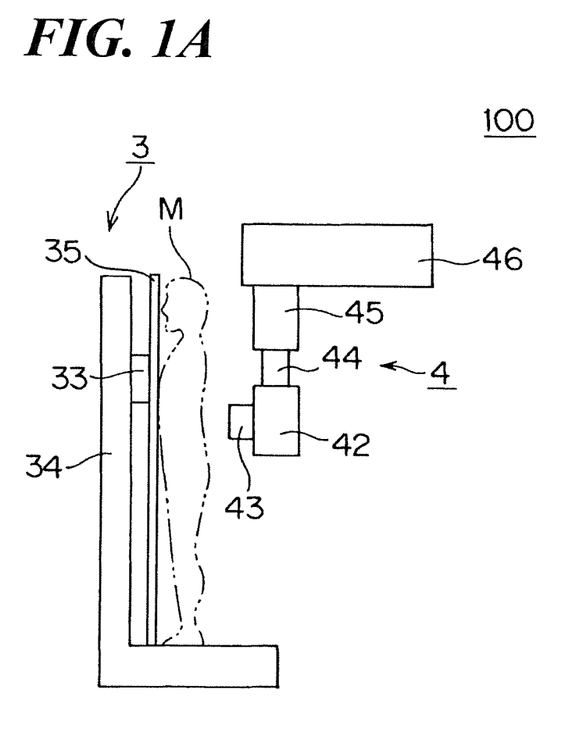
FIG. 1A, FIG. 1B are schematic views of an X-ray imaging apparatus according to an aspect of the present invention.
Figure 1B:
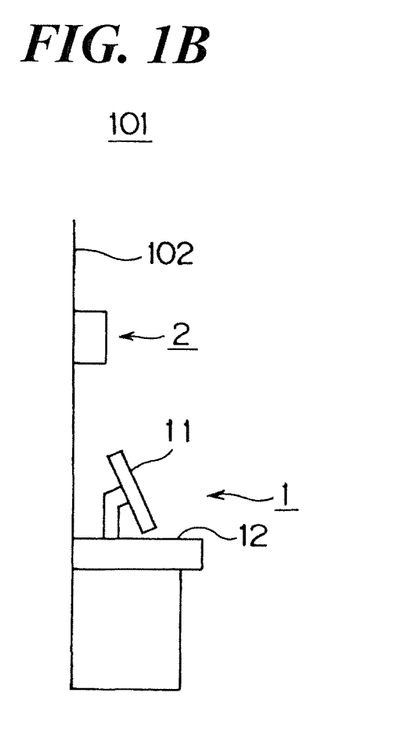
Figure 2:
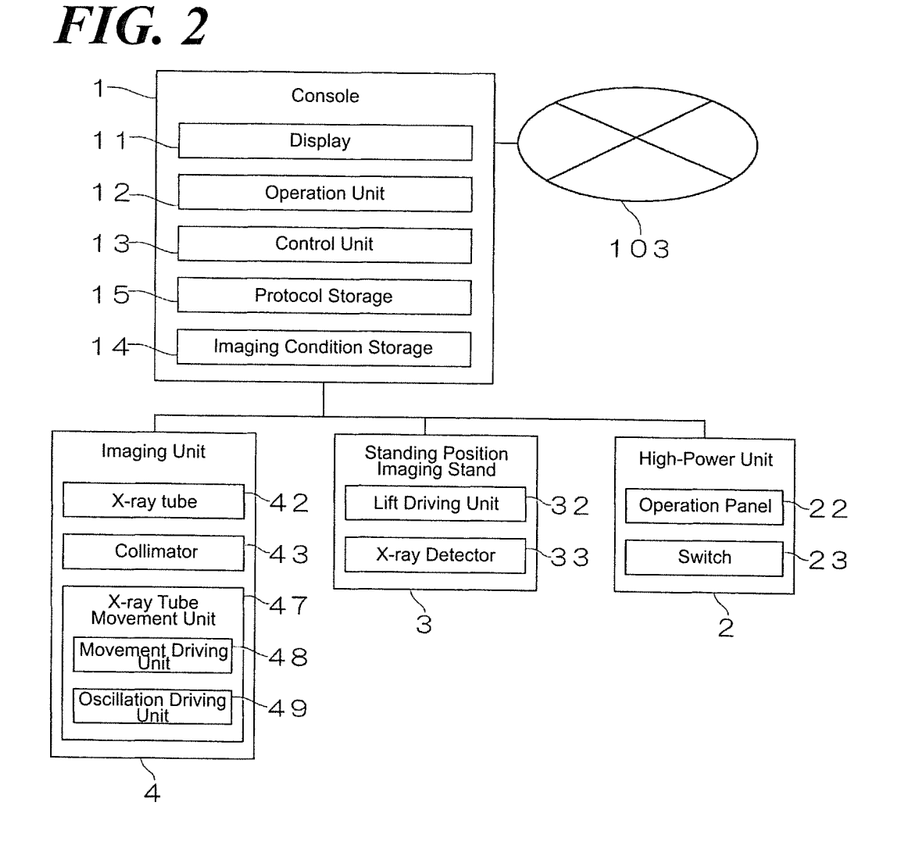
FIG. 2 is a block diagram illustrating the main control system of the X-ray imaging apparatus according to an aspect of the present invention.

The inventors set forth Embodiments of the present invention based on the following FIGs. FIG. 1A, FIG. 1B are schematic views of an X-ray imaging apparatus as the radiation imaging apparatus according to an aspect of the present invention. In addition, FIG. 2 is a block diagram illustrating the main control system of the X-ray imaging apparatus according to the aspect of the present invention.

The X-ray imaging apparatus according to the aspect of the present invention further comprises a console 1 and a high-voltage device 2 that are installed in an operation room 101, in which an operator implements the X-ray imaging operation; and a standing subject imaging stand 3 and an imaging unit 4 that are installed in the imaging room 100 in which the imaging on the subject M is performed. The imaging room 100 and the operation room 101 are separated and blocked by the partition-wall 102.

The console element 1 comprises a display 11 including such as a liquid crystal display and so forth, and an operation unit 12 comprising a keyboard and a mouse and so forth used to execute a variety of operations. The display 11 displays an X-ray imaging image. Referring to FIG. 2, the console 1 further comprises a control unit 13 that controls an entire apparatus. In addition, the console 1 further comprises a protocol storage 15, an imaging condition storage 14 that stores the imaging condition. Such a console 1 is connected with the radiology department information system (RIS) 103 that is an in-house communication relative to the in-hospital subject management system, a variety of information for the X-ray imaging is read out from the radiology department information system (RIS) 103.

In addition, the protocol storage 15 register-and-stores a plurality of protocols used in a series of examinations in order. In addition, the imaging condition storage 14 stores the imaging condition corresponding to each protocol. In addition, instead of storing the plurality of protocols in the protocol storage 15 of the console 1, the plurality of protocols that are used in a series of examinations may be stored in the other connected storage via the radiology department information system 103. In addition, the imaging condition can be read out from the radiology department information system 103 along with the patient information every time when selecting the protocol. Now, the protocol means the information collectively including such as the tube voltage, the electric current, time, the focus size, necessity of a grid, the measurement region and so forth.

A high-voltage device 2 is installed to the partition-wall 102 in the operation room 101. Referring to FIG. 2, the high-voltage device 2 comprises a operation panel 22 including the display element having a touchscreen liquid crystal display; a display panel 22 having an input key (button) and a switch 23 that directs to start an X imaging.

The high-voltage device 2 sets up the X-ray irradiation conditions including the tube voltage and the tube electric current of the X-ray tube 42 and the X-ray irradiation period of time.

Referring to FIG. 1, the standing subject imaging stand 3 comprises a lifting unit 34, which supports the X-ray detector 33 liftably, and a wall stand 35. The X-ray detector 33 is called a Bucky unit comprising such as a flat panel detector (FPD) inside thereof. In addition, referring to FIG. 2, such standing subject imaging stand 3 comprises a lift driving unit 32 that changes a height-position by lift-driving the X-ray detector 33. In addition, the X-ray tube 42 and the collimator 43 constitute a radiation irradiation unit according to the aspect of the present invention and the detector 33 constitutes a radiation detection unit according to the aspect of the present invention.

Referring to FIG. 1, an imaging element 4 comprises: a base 46 movable in the orthogonal direction relative to the ceiling of the imaging room 100; a support column 45 extending downward from the base 46 thereof; a movement element 44 that is telescopic and rotatable relative to the support column 45. The movement unit 44 supports the X-ray tube 42 and the collimator 43. Accordingly, the X-ray tube 42, and the collimator 43 are movable in a unified manner. Accordingly, the X-ray tube 42 and the collimator 43 are oscillable relative to the movement unit 44 in a unified manner. Referring to FIG. 2, the imaging unit 4 comprises an X-ray tube movement unit 47. The X-ray tube movement unit 47 comprises; a movement driving unit 48 that moves the X-ray detector 33 and the collimator 43 in a unified manner by driving-and-controlling a motor (not shown in FIG.), and an oscillation driving unit 49 that oscillates the X-ray tube 42 and the collimator 43 by driving-and-controlling a motor (not shown in FIG.).

Figure 3:
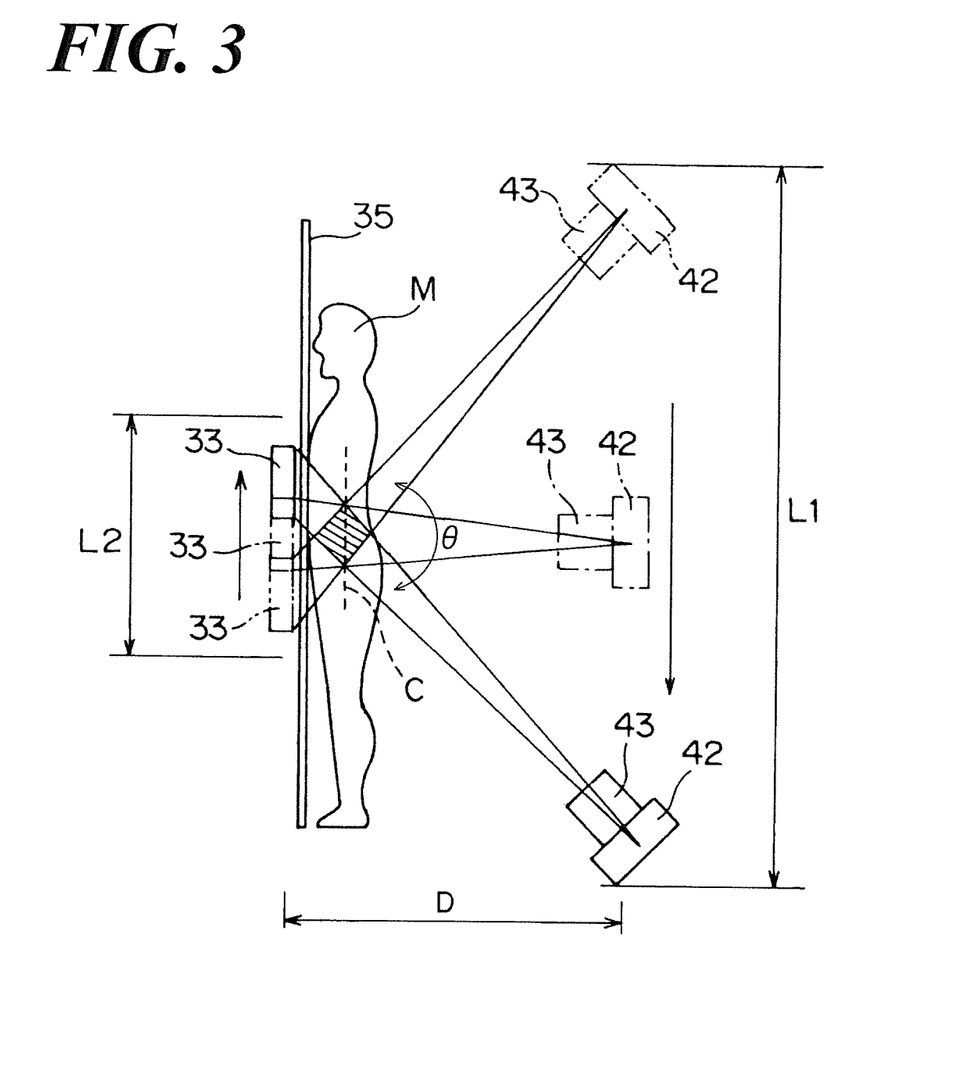
FIG. 3 is a schematic view illustrating the state when performing the tomosynthesis imaging using the X-ray imaging apparatus.

FIG. 3 is a schematic view illustrating the state when performing the tomosynthesis imaging using the X-ray imaging apparatus.

When performing the tomosynthesis imaging on the subject erecting in front of the wall stand (front panel) 35 of the standing subject imaging stand 3, the X-ray tube 42 and the collimator 43 are lowered from the position indicated by the dashed-two dotted line to the position indicated by the solid line via the position indicated by the dashed dotted line in FIG. 3 by driving the movement driving unit 48 in the imaging unit 4 referring to FIG. 2 and also, the X-ray detector 33 is lifted from the position indicated by the dashed-two dotted line to the position indicated by the solid line via the position indicated by the dashed dotted line in FIG. 3 by driving the lifting driving unit 32 of the standing subject imaging stand 3 referring to FIG. 2. And at the same time as the movement operation, the X-ray tube 42 and the collimator 43 are oscillated by driving of the oscillation driving unit 49 of the imaging unit 4 referring to FIG. 2 so that the center-axis of the X-ray irradiated from the X-ray tube 42 faces always the center direction of the X-ray detector 33.

Referring to FIG. 3, the sign L1 denotes the movement range of the X-ray tube 42 and the sign L2 denotes the movement range of the X-ray detector 33. In addition, the sign D denotes the imaging distance. The imaging distance D corresponds to i.e., the distance between the focal point and the image receiving face (SID: Source Image Distance). In addition, the sign θ denotes the tomographic angle that is an irradiation swinging angle to oscillate the X-ray tube 42 and the collimator 43, and the sign C denotes the position of the tomographic center. Further, referring to FIG. 3, the area with hatching is the region of which all X-ray images are generated so as to reconstruct the X-ray tomographic image.

The magnification percentage of the X-ray tomographic image obtained by the tomosynthesis imaging is affected by the imaging distance D. The longer the imaging distance D is, the smaller the magnification percentage of the X-ray tomographic image is, and the shorter the imaging distance D is, the larger the magnification percentage of the X-ray tomographic image is. In addition, the tomographic thickness of the X-ray tomographic image is affected by the tomographic angle θ. The larger the tomographic angle θ is, the thinner the thickness of the X-ray tomographic image is, and the smaller the tomographic angle θ is, the thicker the thickness of the X-ray tomographic image is.

When performing the pre-shot imaging and the tomosynthesis imaging using such an X-ray imaging apparatus as set forth above, the protocol for the per-shot imaging is read out from the protocol storage 15. Reading out the protocol is executed by that the operator operates the operation unit 12 of the console 1. In such a way, according to the present X-ray imaging apparatus, the imaging condition of the protocol for the continuously executed tomosynthesis imaging is read out by the control unit 13 while linking the protocol of the pre-shot imaging. In addition, the imaging condition read out by the control unit 13 is displayed on the display 11.

Specifically, according to the conventional X-ray imaging apparatus, even when the protocol for the pre-shot imaging and the protocol for the tomosynthesis imaging are registered in the temporally-continuous state, only the pre-shot imaging condition is read out and displayed when the protocol for the pre-shot imaging is selected. Whereas, according to the X-ray imaging apparatus of the present invention, when the protocol for the pre-shot imaging is selected, not only the imaging condition relative to the protocol for the pre-shot imaging is read out, but also the imaging condition of the protocol for the tomosynthesis imaging, continuously being executed, is read out in parallel and displayed on the display 11.

The read-out imaging conditions include the imaging distance D and the tomographic angle θ. In addition, the position of the tomographic center C and the imaging period of time for the tomosynthesis imaging are also read out in addition to the imaging distance D and the tomographic angle θ. The read-out imaging conditions are stored in the imaging condition storage 14 of the console 1 and displayed on the display 11. The operator makes sure the imaging conditions on the tomosynthesis imaging on the display 11 and sets up the imaging conditions for the pre-shot imaging so as to be adapted thereinto. In addition, when the X-ray imaging apparatus equips an automatic positioning function, the X-ray tube 42 and the collimator 43, and the X-ray detector 33 automatically move to the desired location.

When reading out the imaging condition of the pre-shot imaging prior to the pre-shot imaging, the imaging condition for the next tomosynthesis imaging is read out and displayed, so that the imaging condition for the pre-shot imaging is set up based on the imaging condition for the tomosynthesis imaging. Therefore, when the tomosynthesis imaging is performed, no more positioning of the X-ray tube and so forth is mandatory again, so that the tomosynthesis imaging is immediately performed.

For example, given the imaging distance D is 120 cm on tomosynthesis imaging, the imaging distance D on the pre-shot imaging is also set up as 120 cm. In addition, according to necessity, the imaging condition for the pre-shot imaging is set up considering other condition including such as a tomographic angle θ on the tomosynthesis imaging, the position of the tomographic center C, the imaging period of time on the tomosynthesis imaging and so forth.

In addition, it is determined whether the movement range of such as the X-ray tube 42 is out of the movable range of such as the X-ray tube 42 or not in the state in which the control unit 13 selects the protocol for the pre-shot imaging based on the read-out imaging condition for the tomosynthesis imaging. Specifically, the control unit 13 determines whether the tomosynthesis imaging is feasible under such conditions or not. As described in Patent Document 2, such a determination is executed by a possible imaging range calculation circuit of the control unit 13, which calculates the possible imaging range of the X-ray detector, which is the positional range of the X-ray detector 33 that can acquire the X-ray tomographic image without that such as the X-ray tube 42 is not going out of the movable range of such as the X-ray tube, based on a group consisting of parameters comprising an imaging distance from the focal point of the X-ray tube 42 to the detection surface of the X-ray detector 33, the irradiation swinging angle that is the swinging angle of the X-ray tube 42 while the X-ray tube 42 is repeating the X-ray irradiation and the movable range of the X-ray tube 42 and so forth.

And when the movement range of such as the X-ray tube 42 is out of the movable range of such as X-ray tube 42, such as an alarm display appears on the display 11 indicating that the imaging is out of order and unfeasible. Accordingly, the operator can recognize that the movement range of such as the X-ray tube 42 is going out of the movable range and change the position of the X-ray tube 42 and other imaging conditions.

As set forth above, according to the X-ray imaging apparatus of the present invention, the imaging positioning of the tomosynthesis imaging is feasible in parallel along with the pre-shot imaging, so that the operator continuously performs the tomosynthesis imaging following carrying out the pre-shot imaging, i.e., without reentering into the imaging room 100. Therefore, the examination time shortens and the burdens on the subject M and the operator decrease.

In addition, according to the aspect of the Embodiment set forth above, the present invention is applied to the X-ray imaging apparatus in which the X-ray detector 33 moves up-and-down, but the X-ray detector 33 can be fixed. In such a case, regardless of the position of the tomographic center that is in-place in the side of the X-ray detector 33, the same effect on the action as the Embodiment set forth above can be obtained.

In addition, according to the aspect of the Embodiment set forth above, the present invention is applied to the X-ray imaging apparatus performing the X-ray imaging for the erecting subject M using the standing subject imaging stand 3, but the present invention is also applicable to the X-ray imaging apparatus performing the X-ray imaging for the lying subject M.

REFERENCE OF SIGNS

1 Console
2 High-voltage unit
3 Standing subject imaging stand
4 Imaging unit
11 Display
12 Operation unit
13 Control unit
14 Imaging condition storage
15 Protocol storage 22 Operation panel
23 Switch
32 Lifting driving unit
33 X-ray detector
42 X-ray tube
43 Collimator
47 X-ray tube movement unit
48 Movement driving unit
49 Oscillation driving unit
100 Imaging room
101 Operation room
103 Radiology department information system
M Subject
D Imaging distance
θ Tomographic angle As used herein, a computerized or computer-type system comprises an input device for receiving data in any form, an output device for outputting data in any form (e.g. data transmission, printing or displaying on a display screen, etc, without limitation), a memory for storing data as well as computer code, and a processor/microprocessor (the same) for executing computer code wherein said computer code resident in said memory to cause the processor/microprocessor to read-in data, process said data within said microprocessor and output said processed data via said output device.

It will be understood that the discussed 'units' or other elements, or detectors, switches, etc. will be understood to be functional as arranged herein without the need for minute disclosure of particular sub-components, resistors, pc-boards, etc.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related radiation imaging devices, computer and operational controls and technologies of radiographic devices and all their sub components, including various circuits and combinations of circuits without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor/microprocessor etc. can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112(f), only when the word 'for' is combined with 'means' in the claim. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A radiation imaging apparatus, comprising:
   a radiation irradiation unit;
   a radiation detector that detects a radiation that is irradiated from the radiation irradiation unit and transmits through a subject; and
   a radiation irradiation unit movement mechanism that moves said radiation irradiation unit in a body axis direction of said subject and oscillates said radiation irradiation unit to adjust a radiation irradiation direction, which is a facing direction to said radiation detector, along with a movement of said radiation irradiation unit;
   wherein the radiation imaging apparatus performs a tomosynthesis imaging that carries out a plurality of imagings relative to said subject while moving said radiation irradiation unit following performing a pre-shot imaging, in which an imaging relative to the subject is carried out while said movement of said radiation irradiation unit is suspending;
   the radiation imaging apparatus further comprising:
   a protocol storage that stores a plurality of protocols corresponding to each said imaging;
   a display that displays an imaging condition corresponding to a presently selected protocol from said plurality of protocols; and
   a control unit that displays said imaging condition for said tomosynthesis imaging on said display along with said imaging condition for said pre-shot imaging when said protocol for said pre-shot imaging is selected in a case of that said pre-shot imaging and said tomosynthesis imaging are registered in a temporally-continuous protocol among said plurality of protocols stored in said protocol storage.

2. A radiation imaging apparatus, comprising:
   a radiation irradiation unit;
   a radiation detector that detects a radiation that is irradiated from the radiation irradiation unit and transmits through a subject; and
   a radiation irradiation unit movement mechanism that moves said radiation irradiation unit in a body axis direction of said subject and oscillates said radiation irradiation unit to adjust a radiation irradiation direction, which is a facing direction to said radiation detector, along with a movement of said radiation irradiation unit;
   wherein the radiation imaging apparatus performs a tomosynthesis imaging that carries out a plurality of imagings relative to said subject while moving said radiation irradiation unit following performing a pre-shot imaging, in which an imaging relative to the subject is carried out while said movement of said radiation irradiation unit is suspending;
   the radiation imaging apparatus further comprising:

a protocol storage that stores a plurality of protocols corresponding to each imaging;

a control unit that determines whether said tomosynthesis imaging is feasible or not in a basis of the imaging condition on said pre-shot imaging by reading out said imaging condition for said tomosynthesis imaging along with said imaging condition for said pre-shot imaging when said protocol for said pre-shot imaging is selected in a case of that said pre-shot imaging and said tomosynthesis imaging are registered in a temporally-continuous protocol among said plurality of protocols stored in the protocol storage.

3. The radiation imaging apparatus, according to claim 1, wherein:

said tomosynthesis imaging condition comprises an imaging distance and a tomographic angle.

4. The radiation imaging apparatus, according to claim 1, wherein:

said tomosynthesis imaging condition comprises an imaging period of time.

5. The radiation imaging apparatus, according to claim 1, wherein:

said tomosynthesis imaging condition comprises a tomographic center.

* * * * *